United States Patent [19]

Slinkard et al.

[11] 4,195,188
[45] Mar. 25, 1980

[54] STEAM ASSISTED HYDROCARBON OXIDATION PROCESS

[75] Inventors: William E. Slinkard, Corpus Christi, Tex.; Anthony B. Baylis, Berkeley Heights, N.J.; Peter B. DeGroot, Corpus Christi; Michael P. Hughes, Odessa, both of Tex.

[73] Assignee: Celanese Corporation, New York, N.Y.

[21] Appl. No.: 859,897

[22] Filed: Dec. 12, 1977

[51] Int. Cl.$^2$ .................. C07C 51/20; C07C 53/08
[52] U.S. Cl. ................................ 562/549; 260/604 R; 585/658; 562/536; 562/542; 562/547; 562/548
[58] Field of Search ............... 260/533 R; 562/549, 562/548, 542, 536

[56] References Cited

U.S. PATENT DOCUMENTS 3,907,833  9/1975  Slinkard et al. .................. 260/533 R

FOREIGN PATENT DOCUMENTS 166670  11/1964  U.S.S.R. ............................ 260/533

Primary Examiner—Vivian Garner
Attorney, Agent, or Firm—Linn I. Grim

[57] ABSTRACT

The present invention provides a highly efficient process for use in the high pressure catalytic vapor phase reaction for the high yield conversion of lower aliphatic hydrocarbons such as n-butane to corresponding monocarboxylic acids such as acetic acid. The oxidation reaction takes place under hydrocarbon rich conditions. The increased efficiency in this process is realized by the judicious use of steam and the catalyst systems set forth in the instant invention.

9 Claims, No Drawings

STEAM ASSISTED HYDROCARBON OXIDATION PROCESS

BACKGROUND OF THE INVENTION

Processes for producing lower aliphatic monocarboxylic acids such as acetic acid by the vapor phase oxidation of lower aliphatic hydrocarbons are known. For example, acetic acid is prepared by the vapor phase oxidation of butane according to the following equation:

$$C_4H_{10} + 5/2\, O_2 \rightarrow 2CH_3COOH + H_2O.$$

However, processes for the oxidation of hydrocarbons in the vapor phase by means of oxygen-containing gases have not proven entirely satisfactory primarily due to the excessive formation of undesirable carbon oxides, and to the difficulty in maintaining control of the highly exothermic oxidation reaction. U.S. Pat. No. 3,395,159 provides an improved process wherein the oxidation of hydrocarbons is performed in a reactor system having fused vanadium oxide catalyst coated on the inner surface of the reactor, which system has the advantage of better temperature control and isothermal operation. The use of early catalysts, such as vanadium pentoxide, either supported or unsupported, for the vapor phase oxidation of lower aliphatic hydrocarbons generally results in yields and process efficiencies which fall substantially short of economic potential. Also, the resulting products are often impure due to a lack of selectivity when such catalysts are employed.

In copending applications Ser. Nos. 859,896; 859,595 and 859,898 catalyst and catalytic processes have been presented which realize superior results in the vapor phase oxidation of lower aliphatic hydrocarbons especially n-butane, however as with all catalytic processes there is always a desire to increase selectivity to the preferred product as opposed to the attendant less desired by-products and to reduce oxidation of the catalyst which oxidation is a negative feature of the instant high pressure reactor process which utilizes an activated catalyst in reduced form.

OBJECTS AND SUMMARY OF THE INVENTION

Accordingly, a general object of the present invention is to avoid or substantially alleviate the above-mentioned problems in a simple and straightforward manner.

A more specific object is to provide a process for the efficient production of acetic acid by the vapor phase oxidation of lower aliphatic hydrocarbons.

Since the improved catalysts which have been proposed for the vapor phase oxidation of lower aliphatic hydrocarbons for the production of acetic acid are in a generally reduced state; a specific object of the instant invention is to lower the susceptibility of the catalyst to oxidation and also to increase the selectivity to the desired product which in the case of normal butane feed, is acetic acid.

These and other objects are achieved by a process for preparing acetic acid by the vapor phase oxidation of a lower aliphatic hydrocarbon such as butane, which process comprises reacting under above atmospheric pressure the lower aliphatic hydrocarbon and an oxygen-containing gas in the vapor phase, in the presence of a catalytic amount of a reduced vanadium oxide catalyst in the presence of steam.

The essence of the invention lies in the discovery that steam, which heretofore has been used in reactions, such as oxidation reactions, for temperature control, i.e., to function as a diluent and control hot spots within the reactor; not only does that in the instant oxidation reaction but also, since the proposed improved catalysts for this oxidation of lower aliphatic hydrocarbons are generally in a reduced state, the steam serendipitously (1) retards the rate of oxidation of vanadium oxides and (2) additionally increases selectivity of the catalyst to the desired end product, i.e., acetic acid. This of course was not realized in the prior art because heretofore the catalyst systems utilized in the vapor phase oxidation of lower aliphatic hydrocarbons were either (1) in a fully oxidized state or (2) the reactions were conducted at atmospheric (or below) pressures wherein the catalyst oxidation does not take place. In low pressure operations, it is believed that the reduction of the catalyst by the butane and the oxidation of the butane by air (or oxygen) vis-a-vis the oxidation of the catalyst by air (or oxygen) is such that deactivation is not a noticeable problem with low temperature operations. Under high pressure operations, maleic acid, which is a by-product formed at the expense of the desired product of acetic acid, goes from a production of about 6% when no steam is present to less than 1% with the addition of steam to the reaction medium.

Other objects and advantages of the present invention will become apparent from the following description of the preferred embodiments.

DESCRIPTION OF THE PREFERRED EMBODIMENTS

In the process of the present invention a lower aliphatic hydrocarbon is reacted with an oxygen-containing gas in the presence of steam and a catalytically effective amount of a reduced vanadium oxide or reduced vanadium pentoxide catalyst to produce acetic acid.

By "lower aliphatic hydrocarbon" is meant any saturated or unsaturated aliphatic hydrocarbon containing from 2 to 10 carbon atoms. These lower aliphatic hydrocarbons include alkanes, alkenes and alkynes such as ethylene, propylene, butene, propane, butane, pentene, octane, and their isomers. Particularly preferred aliphatic hydrocarbons are the alkanes and alkenes including propane, butane, butene, isobutane, isobutene and mixtures thereof.

The production of acetic acid from butane can give particularly advantageous results.

By the term "reduced vanadium oxide or reduced vanadium pentoxide" is meant a vanadium oxide in which the average vanadium ion valency is less than 5. A lower oxidation state of vanadium ions is an essential feature of the present invention catalysts. This is based on the observation that vanadium pentoxide (i.e., a catalyst containing vanadium ions with a valence of 5) is not an active catalyst under the process conditions to be described, and it is, therefore, advantageous to exclude vanadium pentoxide from the catalyst compositions to the greatest extent possible.

The reduced vanadium oxides employed in the catalysts of the present invention are all intermediate in average oxidation states, i.e., between $V_2O_5$ and $V_2O_3$. Although the initial charge can contain $V_2O_5$ and $V_2O_3$, X-ray diffraction studies confirm that vanadium oxide catalysts operable in the process are effectively expressed empirically as $V_3O_5$, $V_4O_7$, $V_5O_9$, $V_6O_{11}$, $V_7O_{13}$, $V_2O_4$ and/or $V_6O_{13}$. The average valence of the vanadium ions in these oxides generally ranges from 3 to about 4.5.

Catalysts can be made by preparing a water soluble salt of vanadium with a multibasic organic acid. A number of multibasic acids may be used to prepare the desired water soluble vanadium salt such as oxalic acid, tartaric acid, succinic acid, citric acid, malonic acid, glutaric acid, adipic acid, lactic acid and the like. The preferred acid is oxalic acid. Techniques for preparing these catalysts are well known. For example, solutions of oxalic acid with water can be added to suspensions of $V_2O_5$ in water with vigorous stirring. Evaporators can be utilized to recover the crystalline salts and said salts decomposed under inert atmosphere with high temperatures.

Another manner of producing catalysts useful in the instant invention is to include a metal oxide additive to increase crush strength. Typical of such a catalyst is one prepared by the addition of about 1 to about 50 mole percent of chromium oxide calculated as chromium (III) oxide to a reduced vanadium oxide. The pre-reduced catalyst compositions can be prepared as taught in copending U.S. application Ser. No. 859,896.

Catalysts can also be prepared by the CO reduction of vanadium pentoxide as taught in copending U.S. application Ser. No. 859,898.

The oxygen necessary as a reactant in the present process may be from practically any molecular oxygen-containing gas such as molecular oxygen or air. Also, the molecular oxygen-containing gas may be one wherein molecular oxygen is mixed in varying amounts with an inert diluent gas such as nitrogen, argon, or a carbon oxide. The lower aliphatic hydrocarbon and oxygen-containing gas can be reacted within a wide range of molar ratios. However, it is an essential feature of the invention process that the quantity of oxygen gas in the feed stream be the least required to convert efficiently the hydrocarbon stream to acetic acid consistent with necessary temperature control and retention of catalyst activity. It is important that the vanadium oxide catalyst is not oxidized to vanadium pentoxide. Even the presence of a small amount of vanadium pentoxide is effective in reducing the yield of acetic acid. The quantity of oxygen gas in the feed stream usually is maintained in the range between about 0.05 and 1 moles per mole of lower aliphatic hydrocarbon, e.g., in a molar ratio of oxygen to lower aliphatic hydrocarbon of 0.05 to 0.3.

The essence of the instant invention is the introduction of water which should generally be included in the feed stream in a quantity between about 0.1 and 2.0 moles per mole of lower aliphatic hydrocarbon, typically between 0.3 and 1.5 moles, and preferably between 0.5 and 1.2 moles. The presence of water vapor in the high pressure, hydrocarbon rich oxidation reaction system can increase the yield of acetic acid by as much as 10% in the case where the hydrocarbon feed stream is normal butane.

The present process should be carried out above atmospheric pressures, generally from greater than 1 to about 50 atmospheres, typically from greater than about 1 to about 30 atmospheres, and preferably from greater than about 5 to about 20 atmospheres.

It is, of course, highly desirable to operate the instant process under high pressure conditions for then simple cooling can render the recycle stream of butane and butene and the take-off stream of acetic acid liquid. Furthermore, high pressure operation realizes higher butane oxidation rates.

With experiments conducted at atmospheric pressure, no catalyst oxidation was apparent even when the reactor temperatures were as low as 220° C. However, when high pressure operation was commenced, as mentioned before, the ability to obtain decreased selectivities to carbon oxides, by decreasing temperature in oxidizing $C_4$ hydrocarbons over reduced vanadium catalysts was limited due to a competing reaction of catalyst oxidation and therefore deactivation, at low temperatures.

In the pressure range of from about 5 to about 10 atmospheres, significant catalyst oxidation may occur from about 220° to about 240° C. Deactivation is detectable in the 240° to 250° C. transition range. However, in reactor runs above 250° C., the catalysts of the instant invention appear to be stable to oxidation under given reaction conditions.

Therefore, the present process is carried out at a temperature generally between about 220° and about 400° C., typically from greater than about 240° C. to about 350° C., and preferably from greater than 250° C. to about 300° C.

The contact time of the reactants with the catalyst is generally between about 0.1 and 100 seconds, typically between about 0.25 and 50 seconds. By contact time as used herein, is meant the contact time adjusted to 25° C. and 1 atmospheric pressure (i.e., standard temperature and pressure, denoted STP). Thus, the contact time is calculated by dividing the volume of the catalyst bed (including voids) by the volume per unit time flow rate of the reactants at STP.

The process of the present invention may be carried out continuously and the catalyst may be present in various forms such as in one or more fixed beds or as a fluidized system.

Portions of the reactants which do not undergo reaction may be recycled if necessary. Selected intermediate products, such as butenes and acetaldehyde, are preferably recycled also. The desired acetic acid product may be separated from any impurities by condensation followed by fractionation and aqueous or non-aqueous extraction of the product from the unreacted lower aliphatic hydrocarbon.

In this specification, the terms conversion and efficiency are defined as follows:

$$\text{conversion, \%} = \frac{\text{moles lower aliphatic hydrocarbon or oxygen converted}}{\text{moles lower aliphatic hydrocarbon or oxygen fed}} \times 100$$

% carbon efficiency to component $i$ =
$$\frac{\text{moles component } i \text{ formed} \times \text{carbon atoms per mole of component } i}{\text{total moles of carbon in all products analyzed}} \times 100$$

Acetic acid is generally produced by the present process with a conversion (based on oxygen) generally of at least 90 percent, often at least about 95 percent, a conversion based on lower aliphatic hydrocarbon (which, as noted above, is present in substantial excess) generally of at least about 1 percent, typically from about 3 to about 5 percent, and a carbon efficiency of generally at least about 50 percent, typically at least about 55 percent, often at least about 60 percent with recycled intermediates.

The recovery of the product stream and the separation of the acetic acid from the acetaldehyde, maleic acid and other by-products can be accomplished by conventional procedures. U.S. Pat. No. 3,624,148 describes a method for the separation of acetic acid from maleic acid.

The present invention is further illustrated by the following examples. All parts and percentages in the examples as well as in the specification and claims are by weight unless otherwise specified. The reactants and other specific ingredients are presented as being typical, and various modifications can be devised in view of the foregoing disclosure within the scope of the invention.

The following three comparative examples illustrative the effect of steam in the lower aliphatic hydrocarbon oxidation process.

EXAMPLES I-III

A ¼ inch steel pipe (0.36 inch inside diameter) in a U-shaped configuration is employed to hold the catalyst charge with the catalyst contained in the down flow feed leg. The U-shaped pipe is about 30 inches high. The catalyst charge is about 3cc of $-20+30$ mesh catalyst particles (about 0.5 to 0.9 mm in diameter). The reactor is heated to the desired temperature using a fluidized sand bath. Flow rates of the low aliphatic hydrocarbons and air (or oxygen) are determined at normal temperatures and pressures (STP) using calibrated mass flow meters. Steam is introduced as water at a known flow rate and flashed to steam with the flow rate of steam calculated by application of the ideal gas law. After the reactor with the catalyst charge is installed in the system, the lower aliphatic hydrocarbons and air (or oxygen) and steam mixture is immediately diverted through the catalyst to minimize any oxidation of the catalyst. After the flow rates are stabilized, the temperature of the sand bath (initially about 240° C.) is then raised until the desired oxygen conversion is obtained. Material balances are then obtained at the temperature.

Analysis of the vent gas entails passing the reaction products plus unreacted lower aliphatic hydrocarbons and steam through a water-cooled condenser after leaving the heated reaction zone to remove the liquid products and water from the vent stream. The vent stream leaving the condenser, now containing primarily lower aliphatic hydrocarbons, carbon oxides, and nitrogen (if air was used) is analyzed by standard gas chromatographic techniques. Components analyzed for include butane, butenes, acetaldehyde, oxygen, nitrogen, carbon monoxide, and carbon dioxide. The liquid product is collected at the end of the run and analyzed by standard gas chromatographic techniques. Components analyzed for include: acetic acid, acetaldehyde, propionic acid, maleic acid, formic acid, formaldehyde, acetone, methyl ethylketone, butyric acid, and acrylic acid.

The catalyst used consisted of a commercially purchased sample of vanadium tetroxide, $V_2O_4$, from Rocky Mountain Research Co. mixed with 1 weight percent graphite, pressed into wafers, and then crushed and screened to $-20+30$ mesh particles.

The following represents typical results illustrating the effect of steam in the feed. The two examples are run consecutively with the same identical catalyst charge both with and without steam in the feed. In the without steam case, carbon dioxide was added in the same concentration as steam to approximate the same diluting and heat transfer properties of steam.

|  | With Steam | Without Steam | With 1/10 Steam |
|---|---|---|---|
| Reactor Pressure, psig | 140 | 140 | 140 |
| Reactor Temperature, °C. | 252 | 252 | 251 |
| Feed Stream, Mole Ratio |  |  |  |
| $C_4:O_2:H_2O:CO_2$ | 5.9:1.0:5.4:0.0 | 5.6:1.0:0.0:5.1 | 5.4:1.0:0.4:4.6 |
| Total Feed Rate cc/min (STP) | 117 | 117 | 117 |
| Catalyst Contact Time Seconds (STP) | 1.5 | 1.5 | 1.5 |
| Butane Conversion, % | 5.5 | 4.9 | 5.5 |
| Oxygen Conversion, % | 99 | 99 | 99 |
| Carbon Efficiency, % |  |  |  |
| Butenes | 17 | 14 | 17 |
| Acetic Acid | 47 | 41 | 40 |
| Acetaldehyde | 3.0 | 1.7 | 3.7 |
| Carbon Oxide | 31 | 43 | 38 |

EXAMPLES IV-VI

The catalyst used consisted of a commercially purchased sample of vanadium tetroxide, $V_2O_4$, from Rocky Mountain Research Co. mixed with 1 weight percent graphite and pressed into pellets (⅛ inch diameter × 3/16 inch length). In the next three examples the amount of steam is decreased while the amount of butane present is increased just enough to maintain a constant feed rate to the reactor and a constant contact time over the catalyst. On an equal volume basis butane has a higher heat capacity than water, therefore, if water has only a diluting or temperature moderating effect there should be no change in acetic acid efficiency. As can be seen from the results, this is not the case.

| Reactor Pressure, psig | 140 | 140 | 140 |
|---|---|---|---|
| Reactor Temperature, °C. | 259 | 260 | 260 |
| Feed Stream (Mole Ratio) |  |  |  |
| $C_4°:O_2:H_2O$ | 8.3:1.0:8.5 | 8.2:1.0:4.3 | 8.2:1.0:2.8 |
| Total Feed Rate, l/min (STP) | 27.61 | 27.25 | 27.07 |
| Catalyst Contact Time Seconds (STP) | 0.94 | 0.95 | 0.95 |
| Butane Conversion, % | 3.9 | 3.8 | 3.5 |
| Oxygen Conversion, % | 99 | 99 | 99 |
| Carbon Efficiency, % |  |  |  |
| Butene | 14 | 13 | 14 |
| Acetic Acid | 50 | 47 | 45 |
| Acetaldehyde | 4.9 | 6.2 | 4.2 |
| Carbon Oxides | 29 | 33 | 36 |

EXAMPLES VII–XI

Effect of Water on Vanadium Oxide Oxidation/Reduction Rate

The catalyst used in the oxidation experiments is a reduced vanadium oxide prepared by the calcination of vanadyl oxalate under nitrogen at 425° C. The $V_2O_5$ used in the reduction experiments is the same catalyst heated to 800° C. overnight and then ground in a mortar.

Oxidation and reduction rate experiments are performed on a du Pont 900/950 DTA/TGA apparatus. About 20–30 mg of catalyst or $V_2O_5$ is placed in a tared platinum sample bucket and dried to a constant weight in nitrogen at 100°–140° C. A flow of oxidant or reductant of about 40–100 ml/min is admitted to the sample chamber and the temperature slowly increased to a point where a convenient weight charge per unit time is observed, about 275° C. for oxidation; 350° C. for reduction. The temperature is allowed to stabilize at the selected point and the weight change of the sample is followed for sufficient time to obtain the slope in the region corresponding to an average stoichiometry between $V_2O_{3.7}$ and $V_2O_{4.3}$.

| Oxidation Atmosphere | Temperature, °C. | (mg-atom O) Rate (g-atom V, min) |
| --- | --- | --- |
| air | 275 | 3.08 |
| 3.0 volume % H$_2$O in air | 275 | 1.04 |
| 3.2 volume % H$_2$O in air | 275 | 0.61 |
| Reduction | | |
| n-butane | 350 | −14.2 |
| 3.2 volume % H$_2$O in n-butane | 350 | −22.1 |

As can be seen from the above, water in the butane vapor phase oxidation feed also serves the purpose of helping to stabilize the reduced vanadium oxide state needed for an efficient catalyst and to prolong catalyst life by increasing the reductive capacity of the excess butane and reducing the oxidative capacity of the oxygen in the feed gas; a phenomenon of critical importance in above-atmospheric hydrocarbon-rich, n-butane reaction conditions.

We claim:

1. A process for preparing acetic acid by the vapor phase oxidation of lower aliphatic hydrocarbons which process comprises reacting alkanes having 2–10 carbon atoms with an oxygen-containing gas in the vapor phase above atmospheric pressure at from about 220°–400° C. in the presence of a catalytic amount of a catalyst consisting essentially of a reduced vanadium oxide and steam wherein the molar ratio of steam to alkane is from about 0.1 to 2.0 and the molar ratio of oxygen to alkane is from about 0.05 to 1.0.

2. The process of claim 1 wherein the molar ratio of steam to alkane is from about 0.5 to about 1.2.

3. The process of claim 1 wherein the molar ratio of oxygen to alkane is from about 0.05 to 0.30.

4. The process of claim 1 wherein the pressure of the process is from greater than about 5 to about 20 atmospheres.

5. The process of claim 1 wherein the alkane is n-butane.

6. The process of claim 1 wherein the alkane feed stream contains recycled butene.

7. The process of claim 1 wherein the alkane feed stream contains recycled butene and acetaldehyde.

8. The process of claim 1 wherein the temperature of the process is from greater than 240° C. to about 350° C.

9. The process of claim 1 wherein the temperature of the process is from greater than 250° C. to about 300° C.

* * * * *